US012765979B2

(12) United States Patent
Kim et al.

(10) Patent No.: US 12,765,979 B2
(45) Date of Patent: Oct. 20, 2026

(54) ORAL MODEL DATA MATCHING METHOD AND DEVICE

(71) Applicant: OSSTEM IMPLANT CO., LTD., Seoul (KR)

(72) Inventors: Ah Reum Kim, Seoul (KR); Jong Moon Kim, Gunpo-si (KR); Jin Woong Kim, Incheon (KR); Hyo Jeong Kim, Seoul (KR); Sang Hyeong Cho, Seoul (KR); Kyoo Ok Choi, Seoul (KR)

(73) Assignee: OSSTEM IMPLANT CO., LTD., Seoul (KR)

( * ) Notice: Subject to any disclaimer, the term of this patent is extended or adjusted under 35 U.S.C. 154(b) by 1119 days.

(21) Appl. No.: 17/796,146

(22) PCT Filed: Jan. 28, 2021

(86) PCT No.: PCT/KR2021/001122
§ 371 (c)(1),
(2) Date: Jul. 28, 2022

(87) PCT Pub. No.: WO2021/157948
PCT Pub. Date: Aug. 12, 2021

(65) Prior Publication Data

US 2023/0076682 A1 Mar. 9, 2023

(30) Foreign Application Priority Data

Feb. 3, 2020 (KR) ........................ 10-2020-0012357

(51) Int. Cl.
*A61C 13/34* (2006.01)
*A61B 90/00* (2016.01)
(Continued)

(52) U.S. Cl.
CPC .............. *A61C 13/34* (2013.01); *A61B 90/39* (2016.02); *G06F 30/20* (2020.01); *G16H 30/20* (2018.01); *A61B 2090/3937* (2016.02)

(58) Field of Classification Search
CPC ..... A61C 13/34; A61C 1/084; A61C 13/0004; A61C 9/0053; A61C 9/004; A61C 9/0046;
(Continued)

(56) References Cited

U.S. PATENT DOCUMENTS

| | | | |
|---|---|---|---|
| 8,805,658 | B2 | 8/2014 | Pettersson et al. |
| 10,952,814 | B2 | 3/2021 | Kim et al. |

(Continued)

FOREIGN PATENT DOCUMENTS

| | | | |
|---|---|---|---|
| CN | 109152620 | A | 1/2019 |
| CN | 112294467 | A | 2/2021 |

(Continued)

OTHER PUBLICATIONS

Extended European search report issued on Jan. 19, 2024, in counterpart European Patent Application No. 21750824.1 (9 pages).

(Continued)

*Primary Examiner* — Courtney D Heinle
*Assistant Examiner* — Andrew Thanh Bui
(74) *Attorney, Agent, or Firm* — NSIP Law

(57) ABSTRACT

The present disclosure relates to a method and device for matching oral model data that can provide matching points to a user to match oral model data and computerized tomography (CT) data even for edentulous patients. In this way, convenience is increased and matched data can be effectively generated even for edentulous patients for whom matching has been difficult conventionally.

12 Claims, 18 Drawing Sheets

(51) Int. Cl.
*G06F 30/20* (2020.01)
*G16H 30/20* (2018.01)

(58) Field of Classification Search
CPC . A61B 90/39; A61B 2090/3937; A61B 6/032; A61B 6/51; G16H 30/20; G06F 30/20; G06T 2207/30036
See application file for complete search history.

(56) References Cited

U.S. PATENT DOCUMENTS

| | | | |
|---|---|---|---|
| 2009/0263764 A1 | 10/2009 | Berckmans, III et al. | |
| 2010/0305435 A1 | 12/2010 | Magill | |
| 2011/0008751 A1* | 1/2011 | Pettersson | A61C 5/77 433/167 |
| 2011/0045431 A1 | 2/2011 | Groscurth et al. | |
| 2011/0060558 A1 | 3/2011 | Pettersson et al. | |
| 2012/0282567 A1* | 11/2012 | Nilsson | A61C 13/0004 433/68 |
| 2013/0308843 A1 | 11/2013 | Tank | |
| 2016/0106517 A1 | 4/2016 | Groscurth et al. | |
| 2019/0151046 A1 | 5/2019 | Kim et al. | |
| 2021/0030378 A1 | 2/2021 | Heo et al. | |

FOREIGN PATENT DOCUMENTS

| | | |
|---|---|---|
| EP | 2 103 276 A1 | 9/2009 |
| EP | 2 103 276 B1 | 6/2019 |
| JP | 2011-514225 A | 5/2011 |
| JP | 5444322 B2 | 3/2014 |
| KR | 10-1473192 B1 | 12/2014 |
| KR | 10-1538097 B1 | 7/2015 |
| KR | 10-1554157 B1 | 9/2015 |
| KR | 10-2016-0027433 A | 3/2016 |
| KR | 10-1608017 B1 | 4/2016 |
| KR | 10-1631256 B1 | 6/2016 |
| KR | 10-2019-0031711 A | 3/2019 |
| KR | 10-2067614 B1 | 1/2020 |
| WO | WO 2009/115283 A1 | 9/2009 |
| WO | WO 2021/025355 A1 | 2/2021 |

OTHER PUBLICATIONS

Chinese Office Action issued on May 10, 2024, in counterpart Chinese Patent Application No. 202180012414.4 (5 pages in English, 11 pages in Chinese).

"3 Shape Medical A/S Implant Studio". *Manual* (2018). pp. 1-154.

Kim, Yong-Jun, et al. "Application of digital implant system on implant treatment with "all-on-4" concept." *The Journal of Korean Academy of Prosthodontics* vol. 56. Issue 1 (2018). pp. 88-94.

Fang, Jing-Huan, et al. "Digital intraoral scanning technique for edentulous jaws." *The Journal of prosthetic dentistry* vol. 119. Issue 5 (2018). pp. 733-735.

Korean Office Action issued on Jun. 29, 2021 in corresponding Korean Patent Application No. 10-2020-0012357 (6 pages in Korean).

Korean Office Action issued on Dec. 22, 2021 in corresponding Korean Patent Application No. 10-2020-0012357 (5 pages in Korean).

Korean Office Action issued on Apr. 22, 2022 in corresponding Korean Patent Application No. 10-2020-0012357 (3 pages in Korean).

Korean Office Action issued on May 25, 2022 in corresponding Korean Patent Application No. 10-2020-0012357 (4 pages in Korean).

* cited by examiner

ORAL MODEL DATA MATCHING METHOD AND DEVICE

CROSS REFERENCE TO RELATED APPLICATIONS

This application is a U.S. National Stage Application of International Application No. PCT/KR2021/001122, filed on Jan. 28, 2021, which claims the benefit under 35 USC 119(a) and 365(b) of Korean Patent Application No. 10-2020-0012357, filed on Feb. 3, 2020, in the Korean Intellectual Property Office, the entire disclosure of which is incorporated herein by reference for all purposes.

TECHNICAL FIELD

The present disclosure relates to a method and device for matching oral model data, and more particularly, to a method and device for matching oral model data capable of accurately matching oral model data and computerized tomography (CT) data of a patient in order to use the matched data in implant surgery.

BACKGROUND ART

Generally, an implant refers to a replacement that can substitute for a human tissue when an original human tissue is lost. In dentistry, an implant refers to implantation of an artificial tooth. An implant body made of titanium or the like that is not rejected by the human body is placed in an alveolar bone of a lost tooth to replace a lost dental root, and then a crown is mounted on the implant body to form an artificial tooth.

A surgical guide stent is necessary for implant surgery, and in order to manufacture the surgical guide stent, it is necessary to obtain three-dimensional oral model data by scanning the shape of the inside of the oral cavity of the subject, obtain computerized tomography (CT) data by taking a CT scan of the oral cavity of the subject, and then match the three-dimensional oral model data and the CT data.

Matching oral model data and CT data as above allows for a compensation for missing information in each piece of data and for a correction of a distorted part in each piece of data, and thus is very important. However, in the case of an edentulous patient without any maxillary teeth or mandibular teeth, it is difficult to find reference matching points for matching the two pieces of data, and thus there is difficulty in deriving accurate matched data.

DISCLOSURE

Technical Problem

The present disclosure is directed to providing a method and device for matching oral model data capable of accurately matching oral model data and computerized tomography (CT) data for implant surgery.

The present disclosure is also directed to providing a method and device for matching oral model data capable of providing a matching point to allow oral model data and CT data to be matched also for an edentulous patient.

The present disclosure is also directed to providing a method and device for matching oral model data capable of effectively recommending and generating matching points using a computing device.

Objectives of the present disclosure are not limited to the above-mentioned objectives, and other unmentioned objectives should be clearly understood by those of ordinary skill in the art to which the present disclosure pertains from the description below.

Technical Solution

One embodiment of the present disclosure provides an oral model data matching method performed by a computing device, the oral model data matching method including obtaining oral model data which includes markers, modeling a radiographic guide on the basis of the oral model data, obtaining computerized tomography (CT) data on the basis of a result of the modeling, and matching the oral model data and the CT data using the markers.

In one embodiment, the obtaining of the oral model data may include obtaining scan data by scanning an oral model, placing the markers on the scan data, and obtaining the oral model data on the basis of a result of the placing.

In one embodiment, the placing of the markers may include recommending positions on the scan data to place the markers.

In one embodiment, the recommending of the positions on the scan data may include determining candidate areas from the scan data and recommending positions with lowest gradients in the candidate areas as positions to place the markers.

In one embodiment, the recommending of the positions on the scan data may include determining candidate areas from the scan data and recommending central positions of the candidate areas as positions to place the markers.

In one embodiment, the placing of the markers may further include recommending the number of markers to be placed on the scan data.

In one embodiment, the markers may include a first marker which is placed in a front teeth area of the scan data, a second marker which is placed in a right molar area of the scan data, and a third marker which is placed in a left molar area of the scan data.

In one embodiment, all or some of the markers may be grouped, and sizes or heights of the grouped markers may be collectively adjusted.

In one embodiment, the CT data may be CT data on which marker positions that correspond to the markers are indicated.

In one embodiment, the matching using the markers may include matching the oral model data and the CT data by setting end points of the markers and end points of the marker positions as matching points.

In one embodiment, the markers may have a conical shape, a triangular pyramid shape, a quadrangular pyramid shape, a trident shape, or a screw shape.

In one embodiment, the modeling of the radiographic guide may include selecting a plurality of points on the oral model data, connecting the plurality of points to determine a radiographic guide area, and generating a base shape of the radiographic guide on the basis of the determined area.

In one embodiment, the modeling of the radiographic guide may further include generating a shape of a bite index on the basis of the base shape and combining the shape of the bite index with the base shape.

One embodiment of the present disclosure provides an oral model data matching device including a processor, a memory configured to load a computer program executed by the processor, and a storage configured to store the computer program, wherein the computer program includes instructions to perform an operation of obtaining oral model data which includes markers, an operation of modeling a radiographic guide on the basis of the oral model data, an operation of obtaining computerized tomography (CT) data on the basis of a result of the modeling, and an operation of matching the oral model data and the CT data using the markers.

Advantageous Effects

According to various embodiments of the present disclosure, oral model data and computerized tomography (CT) data can be accurately matched and provided for implant surgery.

Also, since matching points can be directly generated and provided for oral model data and CT data, it is possible to effectively generate matched data even for edentulous patients for whom matching has been difficult conventionally.

In addition, since desirable matching points are automatically recommended by a computing device, oral model data can be generated and matched much faster and more effectively.

The advantageous effects of the present disclosure are not limited to those mentioned above, and other unmentioned advantageous effects should be clearly understood by those of ordinary skill in the art from embodiments of the present disclosure.

MODES OF THE INVENTION

Figure 1:
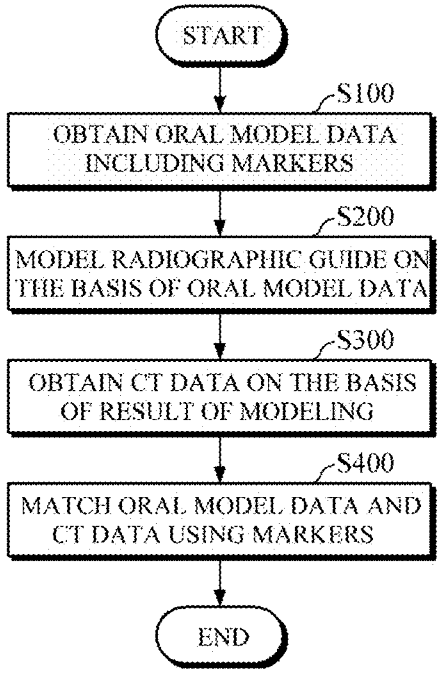
FIG. 1 is a flowchart illustrating an oral model data matching method according to some embodiments of the present disclosure.

Hereinafter, exemplary embodiments of the present disclosure will be described in detail with reference to the accompanying drawings. Advantages and features of the present disclosure and methods of achieving the same should become clear from embodiments described in detail below with reference to the accompanying drawings. However, the present disclosure is not limited to the embodiments disclosed below and may be implemented in various different forms. The embodiments herein only make the disclosure of the present disclosure complete and are provided to completely inform those of ordinary skill in the art to which the present disclosure pertains of the scope of the disclosure. The present disclosure is defined only by the scope of the claims. Like components are denoted by like reference numerals throughout the specification.

Unless otherwise defined, all terms including technical or scientific terms used in this specification have the same meaning as commonly understood by those of ordinary skill in the art to which the present disclosure pertains. Also, terms defined in commonly used dictionaries should not be construed in an idealized or overly formal sense unless expressly so defined herein. Terms used in this specification are for describing the embodiments and are not intended to limit the present disclosure. In this specification, a singular expression includes a plural expression unless the context clearly indicates otherwise.

Hereinafter, some embodiments of the present disclosure will be described with reference to the drawings.

FIG. 1 is a flowchart illustrating an oral model data matching method according to some embodiments of the present disclosure. For example, each step of FIG. 1 is performed by an oral model data matching device implemented using a computing device 500 which will be described below with reference to FIG. 18. Therefore, in the following description, when the subject performing a certain step is not stated, it is assumed that the subject is the oral model data matching device.

In step S100, the oral model data matching device obtains oral model data including markers. Here, the oral model data may be data created by forming markers on data obtained by scanning an inside of an oral cavity of a subject or may be data obtained by attaching markers onto a model (e.g., a plaster model) of an inside of the oral cavity of the subject and scanning the model.

Figure 2:
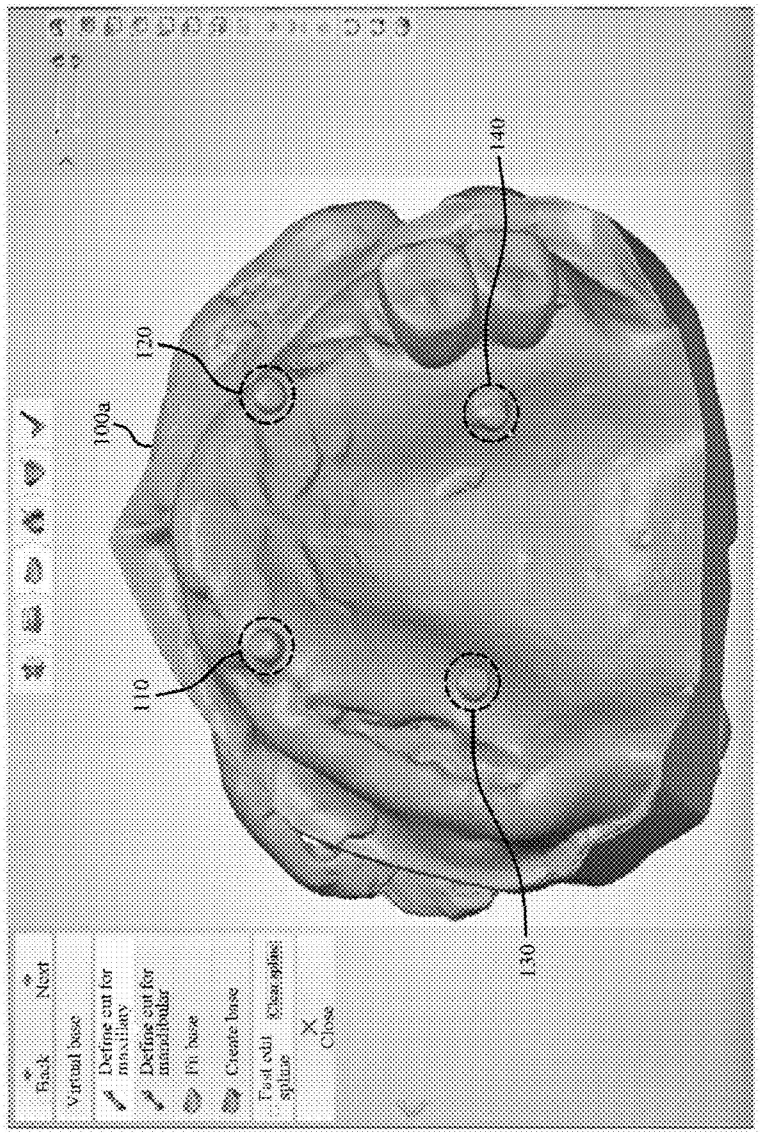
FIG. 2 is an exemplary view of oral model data including markers according to one embodiment of the present disclosure.

An exemplary form of oral model data including markers is illustrated in FIG. 2. Referring to FIG. 2, a plurality of markers 110, 120, 130 and 140 are formed on scan data 100*a* obtained by scanning the inside of the oral cavity of the subject. Since both the oral model data and computerized tomography (CT) data are three-dimensional data, for accurate matching, it is desirable to have three or more matching points if possible. It can be seen that in FIG. 2, a total of four markers 110, 120, 130, and 140, including two markers 110 and 120 placed at a front teeth area, one marker 130 placed at a left molar area, and one marker 140 placed at a right molar area, are formed.

Referring again to FIG. 1, in step S200, the oral model data matching device models a radiographic guide on the basis of the oral model data obtained in the previous step. The radiographic guide is a structure fastened to the oral cavity of the subject to obtain CT data of the subject. The radiographic guide should be made to fit a shape of the inside of the oral cavity of the subject and thus is modeled (or designed) on the basis of oral model data simulating the shape of the inside of the oral cavity.

Figure 3:
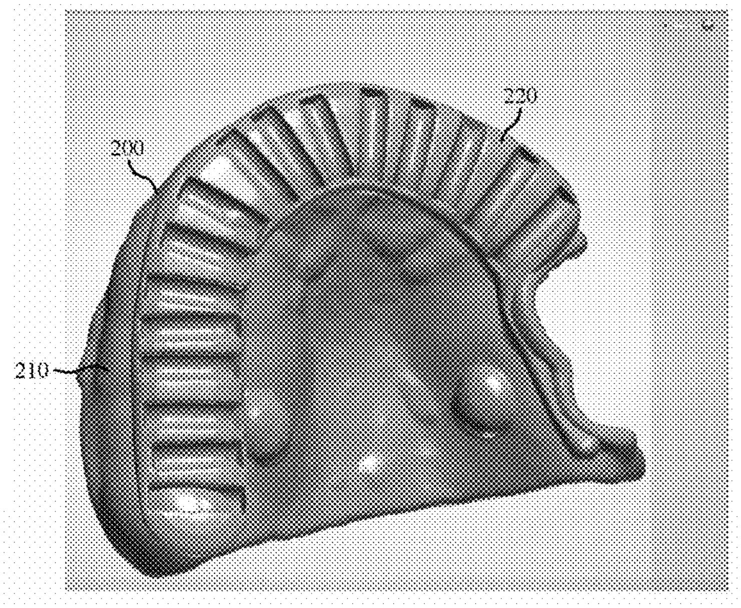
FIG. 3 is an exemplary view of a shape of a radiographic guide modeled on the basis of the oral model data according to one embodiment of the present disclosure.

An exemplary modeled form of the radiographic guide is illustrated in FIG. 3. Referring to FIG. 3, a modeling 200 of the radiographic guide may include a 3D base shape 210 generated on the basis of the oral model data and a bite index shape 220 stacked on the 3D base shape 210. The bite index shape 220 is for forming a bite index on the radiographic guide to be made later, and a bite index is a structure that induces a bite to bind well in a process of aligning an upper jaw, a lower jaw, and the bite of the subject.

When the modeling of the radiographic guide is completed, the radiographic guide is made on the basis of a result of the modeling. Here, for example, the radiographic guide may be made using a method of outputting modeling data with a 3D printer. Also, empty marker sites of the radiographic guide are filled with a radiopaque resin, the radiographic guide is mounted in the subject's oral cavity, and then a CT scan is taken to obtain CT data.

Figure 4:
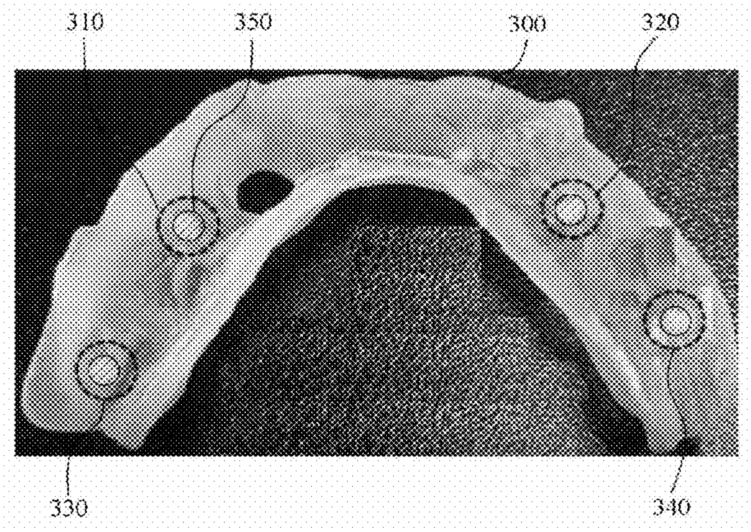
FIG. 4 is a view illustrating a state in which marker sites of the radiographic guide generated according to a modeling result are filled with a resin.
Figure 5:
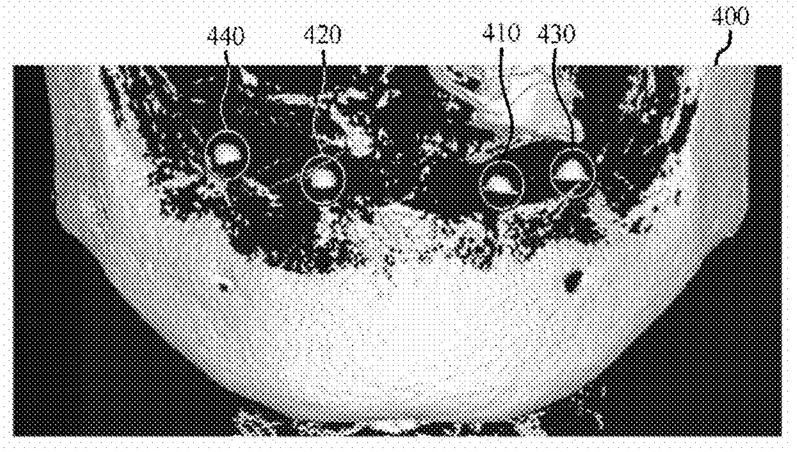
FIG. 5 is an exemplary view of computerized tomography (CT) data obtained using the radiographic guide of FIG. 4.

FIGS. 4 and 5 illustrate exemplary forms of a radiographic guide in which marker sites are filled with a resin and CT data obtained by taking a CT scan using the radiographic guide.

Referring to FIG. 4, it can be seen that empty marker sites 310, 320, 330, and 340 of a radiographic guide 300 made using a 3D printer or the like are filled with a resin 350. Meanwhile, although the material filling the marker sites 310, 320, 330, and 340 is the resin 350 here, the scope of the present embodiment is not limited thereto. The resin 350 is intended to prevent passage of radiation and indicate marker positions on CT data, and thus the resin 350 may be replaced with other radiopaque materials.

Referring to FIG. 5, CT data obtained by fastening the radiographic guide filled with the resin to the subject and taking a CT scan is illustrated. From CT data 400, it can be seen that radiation does not pass through positions where the resin was present, and thus marker positions 410, 420, 430, and 440 are indicated on the CT data 400.

Referring again to FIG. 1, in step S300, the oral model data matching device obtains the CT data. As described above, the obtained CT data is data obtained on the basis of the modeling data of the radiographic guide. The oral model data matching device may be directly connected to a CT scan device and immediately obtain CT data simultaneously upon taking a CT scan or may obtain CT data by receiving previously obtained CT data through a network or a data storage means.

In step S400, the oral model data matching device matches the oral model data and the CT data using the markers of the oral model data and the marker positions of the CT data as matching points. A specific embodiment thereof is illustrated in FIG. 6.

Figure 6:
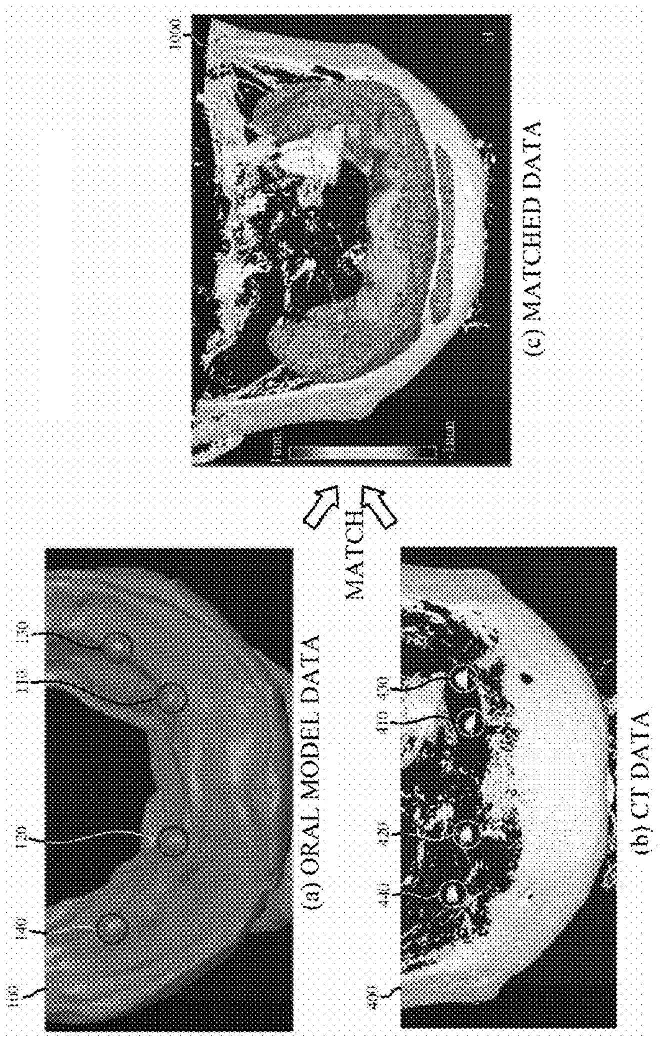
FIG. 6 is a view for describing a method of matching oral model data and CT data using markers.

Referring to FIG. 6, oral model data 100 including the markers 110, 120, 130, and 140 and the CT data 400 on which the marker positions 410, 420, 430, and 440 are indicated are illustrated in (a) and (b), respectively. Here, when the oral model data 100 and the CT data 400 are matched by setting end points of the markers 110, 120, 130, and 140 and end points of the marker positions 410, 420, 430, and 440 corresponding thereto as matching points, matched data 1000 illustrated in (c) may be obtained.

In one embodiment, the markers 110, 120, 130, and 140 may be conical markers. When the markers 110, 120, 130, and 140 have a conical shape, since an end of each of the markers 110, 120, 130, and 140 is indicated by a single point, it may be easier to match the end points of the markers 110, 120, 130, and 140 and the end points of the marker positions 410, 420, 430, and 440.

In one embodiment, the markers 110, 120, 130, and 140 may also be markers of various shapes having a sharp end point other than the conical shape. For example, the markers 110, 120, 130, and 140 may be formed in various shapes with a sharp end such as a triangular pyramid shape, a quadrangular pyramid shape, a trident shape, or a screw shape.

According to the above embodiments of the present disclosure, the oral model data and the CT data can be accurately matched using the markers and the marker positions.

Also, since the markers and the marker positions provided as matching points are newly generated and provided according to the present embodiment, it is possible to effectively generate matched data even for edentulous patients for whom matching has been difficult due to a difficulty of finding matching points.

Figure 7:
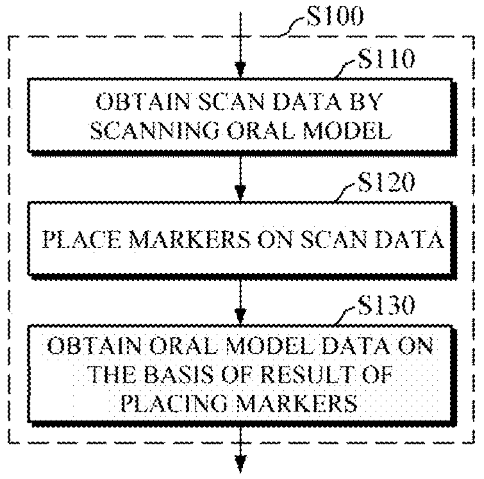
FIG. 7 is a flowchart illustrating one embodiment in which obtaining oral model data (S100) of FIG. 1 is further specified.
Figure 8:
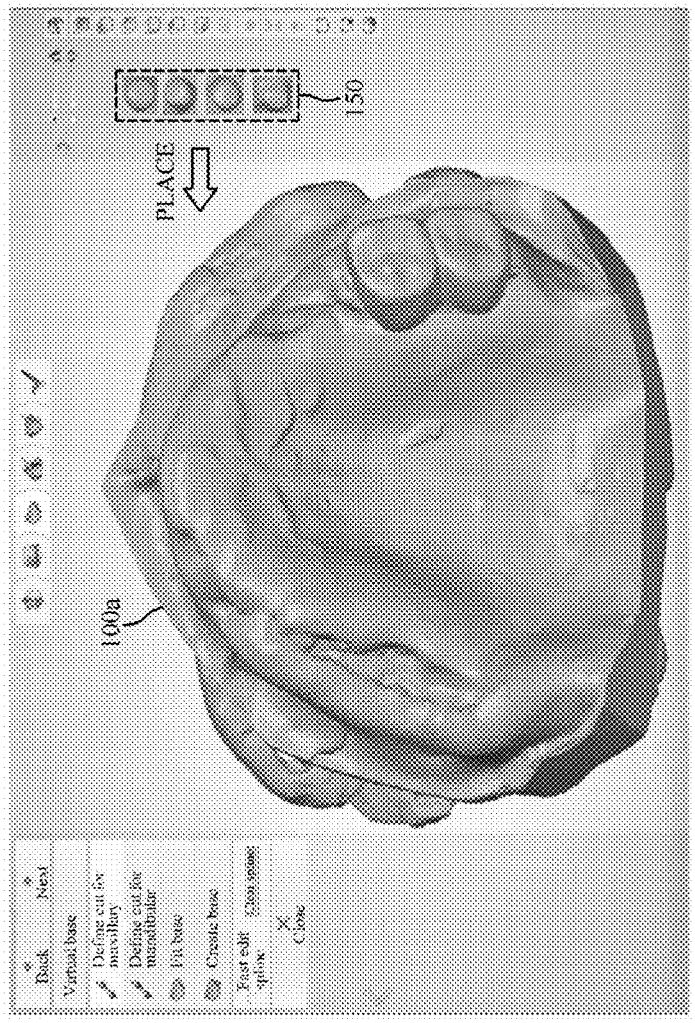
FIG. 8 is a view for describing a method of obtaining oral model data by placing markers on scan data obtained by scanning data of an inside of an oral cavity of a subject.

An embodiment of forming markers on oral model data using a computing device will be described with reference to FIGS. 7 and 8. Hereinafter, FIG. 7 is a flowchart illustrating specific steps of the present embodiment. FIG. 8 is a view conceptually illustrating a specific performing method of the present embodiment. Hereinafter, the embodiment will be described with reference to FIGS. 7 and 8.

In step S110, the oral model data matching device obtains the scan data 100*a* by scanning an oral model. An exemplary form of the scan data 100*a* is illustrated in FIG. 8.

In step S120, the oral model data matching device loads the obtained scan data 100*a* and then calls a marker library (not illustrated) to load markers 150 to be placed on the scan data 100*a*. Then, the oral model data matching device places the markers 150 at appropriate positions on the scan data 100*a*.

In step S130, the oral model data matching device stores the scan data on which the markers are placed and then obtains the oral model data 100 illustrated in FIG. 6 described above.

Figure 9:
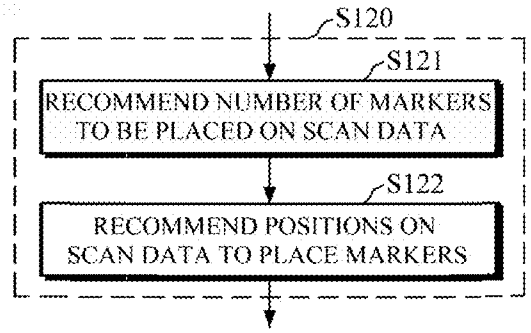
FIG. 9 is a flowchart illustrating one embodiment in which placing markers (S120) of FIG. 7 is further specified.

FIG. 9 is a flowchart illustrating one embodiment in which placing markers (S120) of FIG. 7 is further specified. In the embodiment of FIG. 9, an embodiment of recommending the number of markers to be placed and positions to place the markers is described.

Determining the number of markers to be placed and positions to place the markers on the scan data is very difficult. Of course, it may be easy for a highly-skilled professional medical staff which has accumulated experience and know-how, but guiding an appropriate number of markers and positions to place the markers may allow markers to be formed much more easily and faster.

In step S121, the oral model data matching device recommends the number of markers to be placed on the scan data. Here, the oral model data matching device may determine the number of markers to be recommended based on an area of a region inside an oral cavity, a number of feature points present in the region inside the oral cavity, an external curvature of the oral cavity, or the like based on the scan data. For example, a larger number of matching points may be necessary for accurate matching with the CT data as the area of the region inside the oral cavity gets larger, the number of feature points present in the region inside the oral cavity get fewer, or a degree of the external curvature of the oral cavity gets gentler. Therefore, the oral model data matching device may determine that a larger number of markers is necessary as the area of the region inside the oral cavity gets larger, the number of feature points present in the region inside the oral cavity get fewer, or a degree of the external curvature of the oral cavity gets gentler.

In step S122, the oral model data matching device recommends positions on the scan data to place the markers. Here, the oral model data matching device may recommend the positions to place the markers on the basis of the number of markers recommended in step S121. For example, in a case in which the number of markers recommended in step S121 is three, the oral model data matching device may recommend three positions on the scan data as positions to place the markers.

Meanwhile, in one embodiment, when a user wishes to adjust the sizes or heights of the markers after being recommended the number of markers and the marker positions, the oral model data matching device may group all or some of the markers and apply the same conditions to the grouped markers to collectively adjust the sizes or heights of the grouped markers.

For example, the oral model data matching device may collectively adjust the sizes or heights of the grouped markers to a first value, may collectively adjust the sizes or heights of the grouped markers to increase or decrease by a second value, or may collectively adjust the sizes or heights of the grouped markers to increase or decrease by the same proportion.

Hereinafter, specific embodiments in which the oral model data matching device recommends the positions to place the markers will be described with reference to FIGS. 10 to 13.

Figure 10:
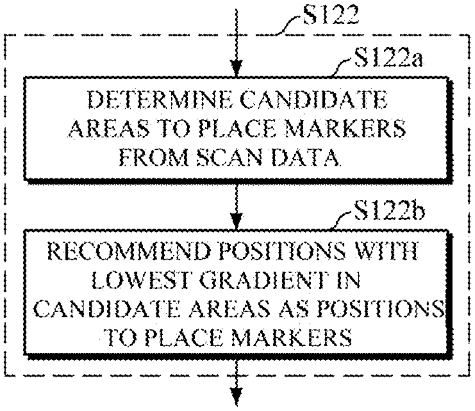
FIG. 10 is a flowchart illustrating one embodiment in which recommending positions on scan data to place markers (S122) of FIG. 9 is further specified.
Figure 11:
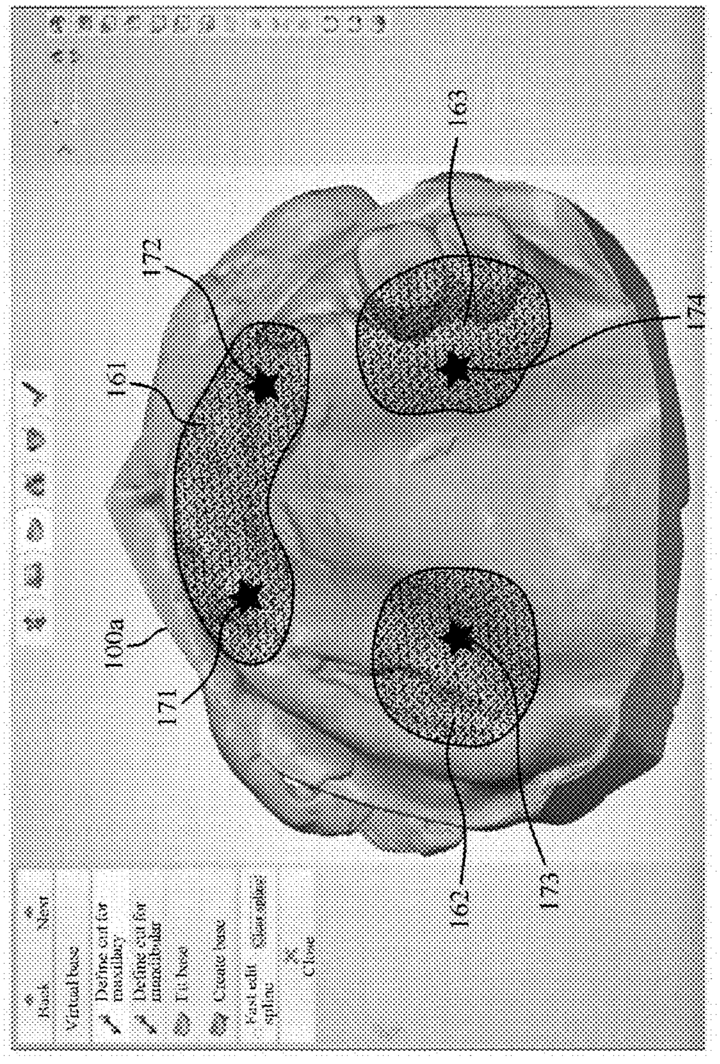
FIG. 11 is a view for describing a method of determining positions to place the markers on the scan data according to the embodiment of FIG. 10.

Referring to FIGS. 10 and 11, as one of the embodiments according to FIG. 9, an example in which the positions to place the markers are recommended on the basis of a gradient of scan data will be described.

In step S122*a*, the oral model data matching device determines candidate areas to place the markers from the scan data. Here, the candidate areas may be determined on the basis of the number of markers recommended in step S121. For example, when the recommended number of markers is three, a single candidate area may be positioned in each of a front teeth area, a left molar area, and a right molar area. Alternatively, when the recommended number of markers is four, two candidate areas may be positioned in any one of the front teeth area, left molar area, and right molar area, and a single candidate area may be positioned in each of the other two. Alternatively, when the recommended number of markers is four, a single candidate area may be positioned in each of the front teeth area, left molar area, and right molar area, and one of the candidate areas may be determined to have a relatively larger area to allow two markers to be placed therein.

In step S122*b*, the oral model data matching device recommends positions with the lowest gradient in the determined candidate areas as the positions to place the markers. Since the markers are used as matching points, it may be desirable to place the markers on conspicuous ridges or deepest valleys if possible. Such ridges or valleys are characteristics mathematically related to the gradient, and when the markers are placed at positions with the lowest gradient in the candidate areas, the markers may be placed at positions closest to a ridge or a valley.

Detailed description thereof will be continued with reference to FIG. 11.

Referring to FIG. 11, three candidate areas 161, 162, and 163 are placed on the scan data 100*a*. Here, when it is assumed that the recommended number of markers is four, a candidate area 161 in the front teeth area is formed to have a relatively larger area than the other candidate areas 162 and 163 to allow two markers to be placed therein.

Then, the oral model data matching device searches for the positions with the lowest gradient for each of the candidate areas 161, 162, and 163. The gradient of each point of the scan data 100*a* may be easily obtained by parsing the scan data 100*a*. Since data parsing is widely known in the art, detailed description thereof will be omitted. For the candidate areas 162 and 163 which are in the molar areas and in which a single marker is placed, the oral model data matching device finds a single point 173 with the lowest gradient for the candidate area 162 and finds a single point 174 with the lowest gradient for the candidate area 163, and for the candidate area 161 which is in the front teeth area and in which two markers are placed, the oral model data matching device finds two points 171 and 172 in the order of the lowest gradient. Also, the oral model data matching device recommends the four found points 171, 172, 173, and 174 as positions to place the markers.

Figure 12:
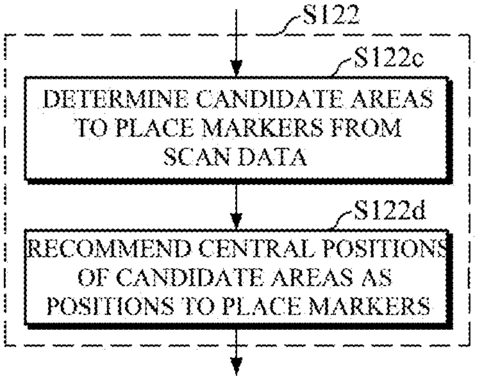
FIG. 12 is a flowchart illustrating another embodiment in which the recommending of the positions on the scan data to place the markers (S122) of FIG. 9 is further specified.
Figure 13:
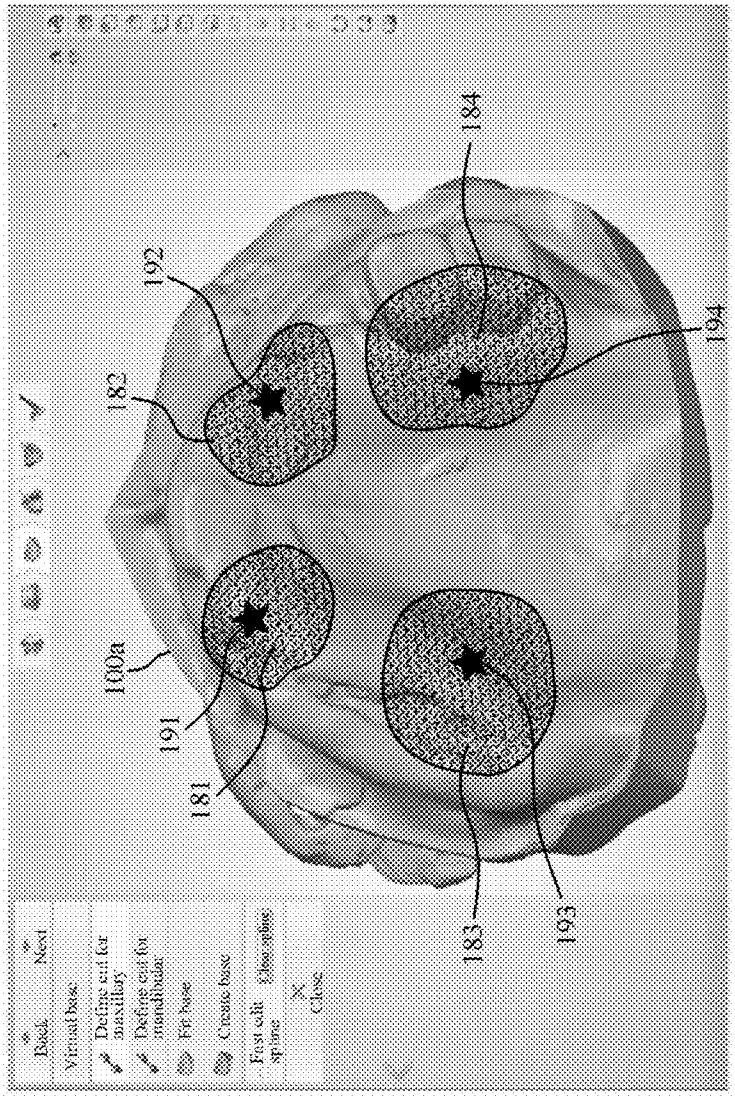
FIG. 13 is a view for describing a method of determining positions to place the markers on the scan data according to the embodiment of FIG. 12.

Referring to FIGS. 12 and 13, as another one of the embodiments according to FIG. 9, an example in which the positions to place the markers are recommended on the basis of central positions of candidate areas will be described.

In step S122*c*, the oral model data matching device determines candidate areas to place the markers from the scan data. Here, the candidate areas may be determined on the basis of the number of markers recommended in step S121. For example, when the recommended number of markers is three, a single candidate area may be positioned in each of the front teeth area, left molar area, and right molar area. Alternatively, when the recommended number of markers is four, two candidate areas may be positioned in any one of the front teeth area, left molar area, and right molar area, and a single candidate area may be positioned in each of the other two. In the present embodiment, since the positions to place the markers are recommended on the basis of the central positions of the candidate areas, a single marker is placed in each candidate area in principle.

In step S122*d*, the oral model data matching device calculates a central position of each candidate area and recommends the calculated central positions as the positions to place the markers. Generally, when selecting a single point that represents a certain area, the center of the corresponding area is selected. In particular, the central position may be considered as a position that best shows the features of the corresponding area in a geometrical aspect. From this viewpoint, the central positions of the candidate areas are recommended as positions to place the markers in the present embodiment. Detailed description thereof will be continued with reference to FIG. 13.

Referring to FIG. 13, four candidate areas 181, 182, 183, and 184 are placed on the scan data 100*a*. Here, when it is assumed that the recommended number of markers is four, the four candidate areas 181, 182, 183, and 184 are set to allow a single marker to be placed in each candidate area. Also, a central position of each of the candidate areas 181, 182, 183, and 184 is calculated. Here, the central position may be defined as a position where a sum of distances to each boundary point is a minimum. When the central position is calculated on the basis of the above, central positions 191, 192, 193, and 194 are determined for the candidate areas 181, 182, 183, and 184, respectively. The oral model data matching device recommends the four determined central positions 191, 192, 193, and 194 as the positions to place the markers.

Figure 14:
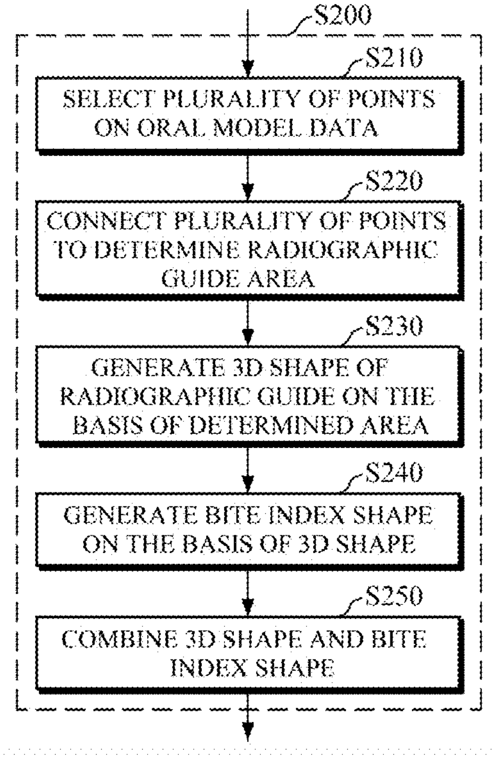
FIG. 14 is a flowchart illustrating one embodiment in which modeling a radiographic guide (S200) of FIG. 1 is further specified.
Figure 15:
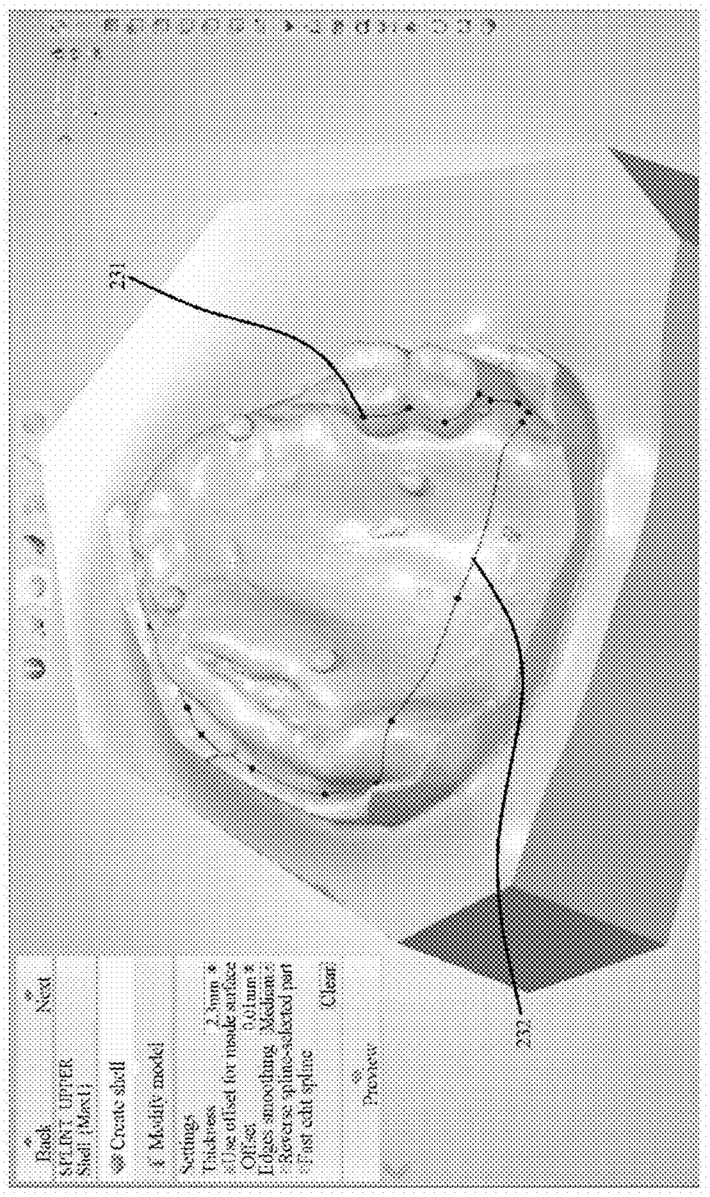
FIGS. 15 and 16 are views for describing a method of determining a radiographic guide area on oral model data.
Figure 16:
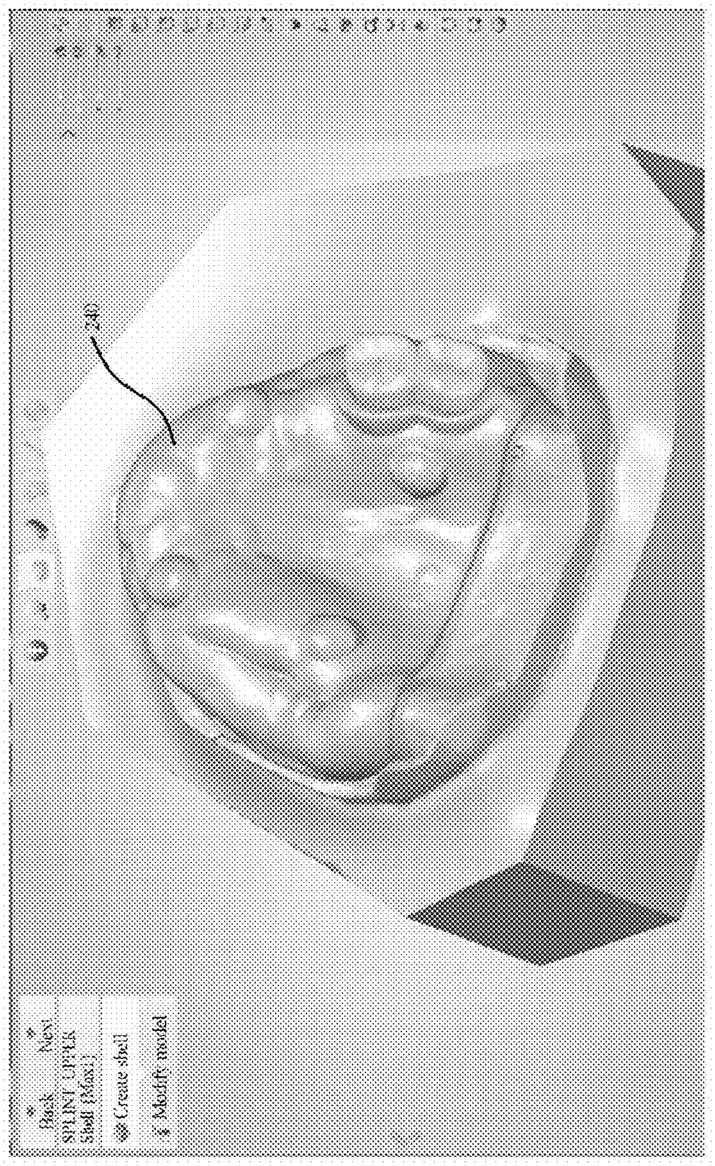
Figure 17:
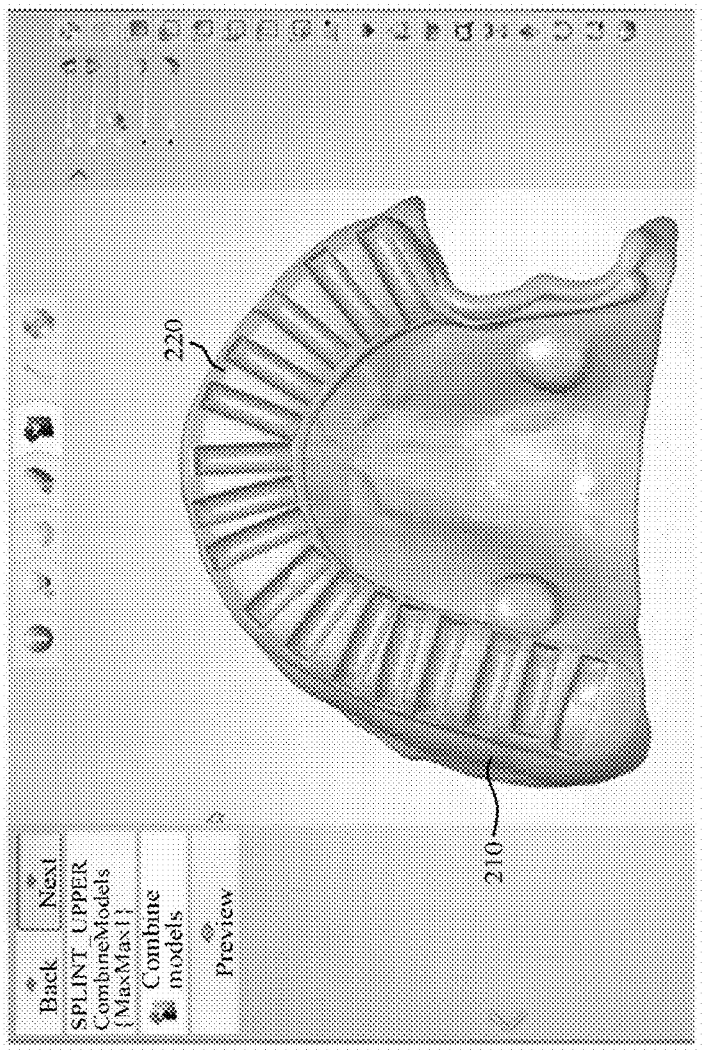
FIG. 17 is a view illustrating a state in which a shape of a bite index is combined with a 3D base shape of the radiographic guide.

FIG. 14 is a flowchart illustrating one embodiment in which the modeling of the radiographic guide (S200) of FIG. 1 is further specified. FIGS. 15 to 17 are conceptual views for schematically describing the process of modeling the radiographic guide. Hereinafter, the present embodiment will be described with reference to FIGS. 14 to 17.

In step S210, the oral model data matching device selects a plurality of points on the oral model data 100. The plurality of points may be selected along an outer boundary portion of the oral model data 100.

In step S220, the oral model data matching device connects the plurality of selected points to determine a radiographic guide area. This will be described with reference to FIG. 15. Referring to FIG. 15, a plurality of points, including a first point 231, which are selected along an outer boundary of oral model data are illustrated. When the plurality of selected points are connected to adjacent points by a line 232, a single closed curve is formed, and the radiographic guide area may be determined using the closed curve as an outer boundary line.

In step S230, the oral model data matching device generates a 3D shape of the radiographic guide on the basis of the determined area. Here, the 3D shape of the radiographic guide is generated to have an outer shape similar to an outer shape of a surface of the oral model data. Referring to FIG. 16, an exemplary form of the 3D shape is illustrated. It can be seen that, for the radiographic guide area determined in step S220, the 3D shape is formed with an outer shape similar to an outer shape of the surface of the oral model data. Due to having an outer shape similar to the outer shape of the surface of the oral model data, the 3D shape of the radiographic guide may also be stacked as it is on top of the oral model data to overlap with the oral model data.

In step S240, the oral model data matching device generates a shape of a bite index on the basis of the generated 3D shape. As described above, the bite index is a structure that induces a bite to bind well in the process of aligning the upper jaw, lower jaw, and bite of the subject. In order to integrally form the bite index with the radiographic guide, the bite index shape 220 is generated together with the 3D base shape 210 of the radiographic guide in the modeling (S200). Referring to FIG. 17, an exemplary form in which the bite index shape 220 is formed on top of the 3D base shape 210 of the radiographic guide is illustrated.

In step S250, the oral model data matching device combines the generated 3D shape and bite index shape to complete the modeling of the radiographic guide. An exemplary form of the completed modeling 200 is illustrated in FIG. 3.

Hereinafter, an exemplary computing device 500 that can implement the oral model data matching device described above in various embodiments of the present disclosure will be described with reference to FIG. 18.

Figure 18:
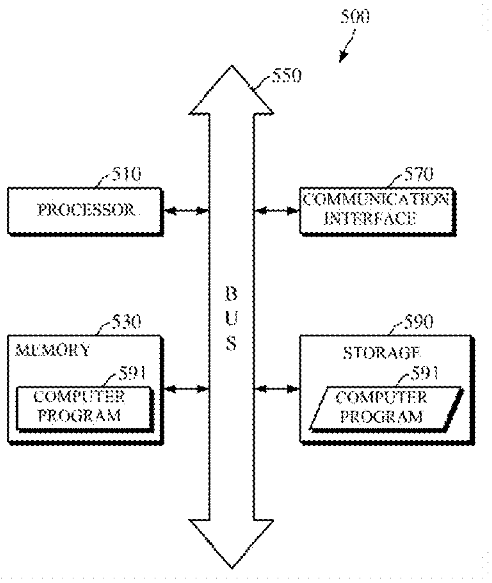
FIG. 18 is a view illustrating a hardware configuration of an exemplary computing device by which various embodiments of the present disclosure can be implemented.

FIG. 18 is an exemplary hardware block diagram illustrating the computing device 500.

As illustrated in FIG. 18, the computing device 500 may include one or more processors 510, a bus 550, a communication interface 570, a memory 530 configured to load a computer program 591 executed by the processors 510, and a storage 590 configured to store the computer program 591. However, only the components relating to the embodiment of the present disclosure are illustrated in FIG. 18. Therefore, those of ordinary skill in the art to which the present disclosure pertains should understand that the computing device 500 may further include general-purpose components other than the components illustrated in FIG. 18.

The processors 510 control the overall operation of each configuration of the computing device 500. The processors 510 may be configured to include at least one of a Central Processing Unit (CPU), a Micro Processor Unit (MPU), a Micro Controller Unit (MCU), a Graphic Processing Unit (GPU), or any other processor widely known in the art to which the present disclosure pertains. Also, the processors 510 may perform an arithmetic operation for at least one application or program for executing methods/operations according to various embodiments of the present disclosure. The computing device 500 may include one or more processors.

The memory 530 stores various pieces of data, commands, and/or pieces of information. The memory 530 may load one or more programs 591 from the storage 590 in order to execute the methods/operations according to various embodiments of the present disclosure. An example of the memory 530 may be a random access memory (RAM), but the memory 530 is not limited thereto.

The bus 550 provides a communication function between the components of the computing device 500. The bus 550 may be implemented as various types of buses such as an address buss, a data bus, and a control bus.

The communication interface 570 supports wired/wireless Internet communication of the computing device 500. The communication interface 570 may also support various communication means other than Internet communication. To this end, the communication interface 570 may be configured to include a communication module widely known in the art to which the present disclosure pertains.

The storage 590 may non-temporarily store one or more computer programs 591. The storage 590 may be configured to include a nonvolatile memory such as a read only memory (ROM), an erasable programmable ROM (EPROM), an electrically erasable programmable ROM (EEPROM), or a flash memory, a hard disk, a removable disk, or any other computer-readable recording media widely known in the art to which the present disclosure pertains.

The computer programs 591 may include one or more instructions implementing the methods/operations according to various embodiments of the present disclosure. For example, the computer programs 591 may include instructions to perform an operation of obtaining oral model data which includes markers, an operation of modeling a radiographic guide on the basis of the oral model data, an operation of obtaining CT data on the basis of a result of the modeling, and an operation of matching the oral model data and the CT data using the markers.

When the computer program 591 is loaded on the memory 530, the processor 510 may execute the one or more instructions to perform the methods/operations according to various embodiments of the present disclosure.

The technical spirit of the present disclosure described above with reference to FIGS. 1 to 18 may be implemented with computer-readable code on computer-readable recording media. Examples of the computer-readable recording media may include removable recording media (a compact disc (CD), a digital versatile disc (DVD), a Blu-Ray disk, a Universal Serial Bus (USB) storage device, or a removable hard disk) or non-removable recording media (a read-only memory (ROM), a random access memory (RAM), or a built-in hard disk). Computer programs recorded in the computer-readable recording media may be sent to other computing devices through a network, such as the Internet, and installed on the other computing devices to be used in the other computing devices.

The embodiments of the present disclosure have been described above with reference to the accompanying drawings, but those of ordinary skill in the art to which the present disclosure pertains should understand that the present disclosure may be embodied in other specific forms without changing the technical idea or essential features thereof. Therefore, the embodiments described above should be understood as being illustrative, instead of limiting, in all aspects. The scope of the present disclosure should be interpreted by the claims below, and any technical idea within the scope equivalent to the claims should be interpreted as falling within the scope of the technical idea defined by the present disclosure.

The invention claimed is:

1. An oral model data matching method comprising:
- obtaining oral model data which includes markers;
- modeling a radiographic guide on the basis of the oral model data;
- obtaining computerized tomography (CT) data with the radiographic guide mounted in a subject's oral cavity; and
- matching the oral model data and the CT data using the markers,
- wherein the obtaining of the oral model data includes:
- obtaining scan data by scanning an oral model;
- determining positions to place the markers and placing the markers on the scan data;
- grouping all or some of the markers and collectively adjusting sizes or heights of the grouped markers; and
- obtaining the oral model data on the basis of a result of the placing.

2. The oral model data matching method of claim 1, wherein the placing of the markers includes recommending positions on the scan data to place the markers.

3. The oral model data matching method of claim 2, wherein the recommending of the positions on the scan data includes:
- determining candidate areas from the scan data; and
- recommending positions with lowest gradients of the scan data in the candidate areas as positions to place the markers.

4. The oral model data matching method of claim 2, wherein the recommending of the positions on the scan data includes:
- determining candidate areas from the scan data; and
- recommending central positions of the candidate areas as positions to place the markers.

5. The oral model data matching method of claim 2, wherein the placing of the markers further includes recommending the number of markers to be placed on the scan data.

6. The oral model data matching method of claim 5, wherein the markers include:
- a first marker which is placed in a front teeth area of the scan data;
- a second marker which is placed in a right molar area of the scan data; and
- a third marker which is placed in a left molar area of the scan data.

7. The oral model data matching method of claim 1, wherein the CT data is CT data on which marker positions that correspond to the markers are indicated.

8. The oral model data matching method of claim 7, wherein the matching using the markers includes matching the oral model data and the CT data by setting end points of the markers and end points of the marker positions as matching points.

9. The oral model data matching method of claim 8, wherein the markers have a conical shape, a triangular pyramid shape, a quadrangular pyramid shape, a trident shape, or a screw shape.

10. The oral model data matching method of claim 1, wherein the modeling of the radiographic guide includes:
- selecting a plurality of points on the oral model data;
- connecting the plurality of points to determine a radiographic guide area; and
- generating a base shape of the radiographic guide on the basis of the determined area.

11. The oral model data matching method of claim 10, wherein the modeling of the radiographic guide further includes:
- generating a shape of a bite index on the basis of the base shape; and
- combining the shape of the bite index with the base shape.

12. An oral model data matching device comprising:
- a processor;
- a memory configured to load a computer program executed by the processor; and
- a storage configured to store the computer program,
- wherein the computer program includes instructions to perform an operation of obtaining scan data by scanning an oral model, an operation of determining positions to place markers on the scan data and placing the markers on the scan data, an operation of grouping all or some of the markers and collectively adjusting sizes or heights of the grouped markers, an operation of obtaining oral model data on the basis of a result of the placing, an operation of modeling a radiographic guide on the basis of the oral model data, an operation of obtaining computerized tomography (CT) data with the radiographic guide mounted in a subject's oral cavity, and an operation of matching the oral model data and the CT data using the markers.

* * * * *